United States Patent [19]

Butler

[11] Patent Number: 4,632,107
[45] Date of Patent: Dec. 30, 1986

[54] HIGH-FREQUENCY JET VENTILATOR
[75] Inventor: Kenneth C. Butler, Carmichael, Calif.
[73] Assignee: Nimbus, Inc., Rancho Cordova, Calif.
[21] Appl. No.: 754,346
[22] Filed: Jul. 11, 1985
[51] Int. Cl.⁴ .............................................. A62B 7/00
[52] U.S. Cl. ........................... 128/204.24; 128/204.25; 137/810; 137/813
[58] Field of Search ...................... 128/200.21, 204.24, 128/204.25, 205.11; 137/810, 812, 813

[56] References Cited
U.S. PATENT DOCUMENTS 3,756,285 9/1973 Johnson et al. ...................... 137/810
4,007,736 2/1977 Schreiber ......................... 128/204.24
4,340,045 7/1982 Manley ........................... 128/204.24

Primary Examiner—Stephen F. Husar
Attorney, Agent, or Firm—Weissenberger and Peterson

[57] ABSTRACT

An opposing vortex oscillator is used to control the frequency and duty cycle of a high-frequency jet ventilator for trauma management in acute and uncontrolled situations where no power other than the pressure of the ventilation gas itself is available. Frequency adjustment is achieved by connecting variable volumes to one inlet of the oscillator while duty cycle control is achieved by supplying fluid to one inlet of the oscillator through a variable-orifice bias control valve. Safety means are provided to automatically disable the ventilator in case of airway blockage.

17 Claims, 5 Drawing Figures

HIGH-FREQUENCY JET VENTILATOR

FIELD OF THE INVENTION

This invention relates to high-frequency jet ventilators, and more particularly to an adjustable ventilator for emergency use in trauma control which requires no power other than the ventilation fluid itself.

BACKGROUND OF THE INVENTION

High-frequency jet ventilation (HFJV) has been clinically demonstrated to be a useful tool in the management of major trauma and cardiopulmonary arrest, particularly as a practical method for emergency airway management in acute, uncontrolled settings. The positive pressure and airflow out of the oropharynx produced by the jet ventilator minimizes aspiration of gastric content, and the low airway pressures produced by HFJV tend to decrease the incidence of tension pneumothorax and impaired central venous return.

Prior art jet ventilators for medical purposes have used externally powered devices such as electric valves to produce the 1-15 Hz pulses of air or oxygen which are introduced into the patient's airway. For emergency use in the field, this is undesirable because of the need for batteries which tend to be heavy and to present reliability problems. In addition, electrical equipment can be dangerous in the presence of flammable fluids which are sometimes present in rescue situations.

It is known that cyclic fluidic pressure pulses can be produced through the use of an opposed vortex oscillator. In the past, such oscillators have been used as sensors for temperature, gas composition, or pressure ratio monitoring applications. In such uses, the oscillator system has a fixed geometry, and changes in the sensed gas parameters alter its frequency.

If an opposed vortex oscillator is used to control a jet ventilator, however, it is necessary for physiological reasons to control the frequency and also the duty cycle of the jet without altering the above parameters. It is with this requirement that the present invention is concerned.

SUMMARY OF THE INVENTION

The invention provides a high-frequency jet ventilator which is fully adjustable as to both frequency and duty cycle, yet which requires no power other than the pressure of the ventilation fluid itself.

The invention achieves its purposes by providing an opposing vortex oscillator which controls an inspiration valve. The frequency of the oscillator can be varied by coupling a variable volume to one input of the oscillator, while the duty cycle can be varied by varying the fluid bias on one of the oscillator inputs.

Preferably, the ventilation fluid itself is used to power the oscillator so that the entire apparatus may be operated from a single fluid source, but a separate fluid supply for the oscillator may be used without departing from the invention.

It is therefore the object of the invention to provide a high-frequency jet ventilator operated entirely by pressurized gas.

It is another object to provide a ventilator of the type described which is adjustable as to both frequency and duty cycle.

It is a further object of the invention to provide means for selectively varying the frequency and duty cycle of an opposed vortex oscillator.

DESCRIPTION OF THE PREFERRED EMBODIMENT

Figure 1:
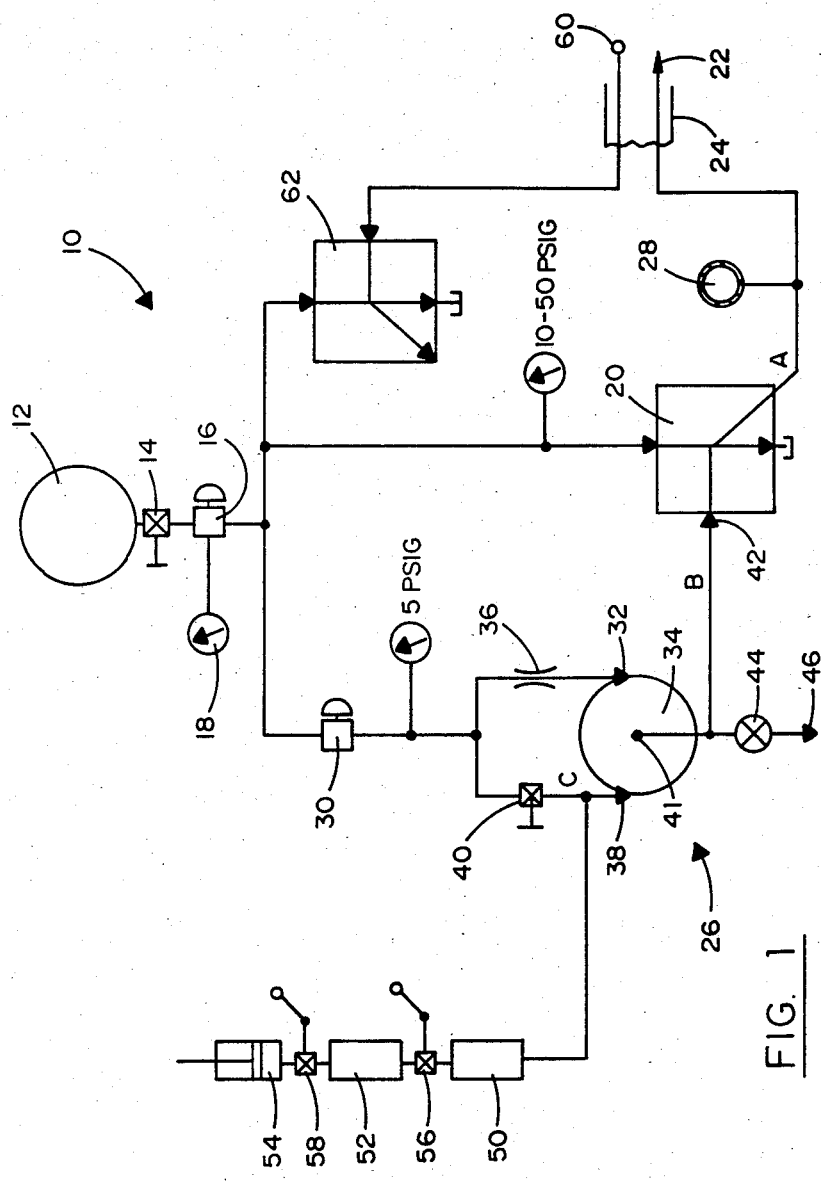
FIG. 1 is a schematic diagram illustrating the jet ventilator of this invention.

In FIG. 1, the ventilator 10 of this invention is shown to include a gas source 12 such as an oxygen bottle, with a shut-off valve 14 and a primary pressure regulator 16. The primary regulator 16, as monitored by the gauge 18, provides sufficient regulation to maintain the input pressure to inspiration valve 20 at a level between about ten and fifty PSIG.

The inspiration valve 20 pulses the jet 22 of the transtracheal introducer 24 as the action of vortex oscillator 26 opens and closes the valve 20 at the rate of about one to fifteen cycles per second. As will be discussed in more detail below, the system of this invention can vary not only the cycling frequency of the valve 20, but also the open/closed ratio (i.e. duty cycle) of each valve cycle. The operation of the jet 22 can be monitored by a visual inspiration indicator 28.

A secondary regulator 30 provides a fixed pressure of about five PSIG to the opposed vortex oscillator 26. This pressure is applied to the right tangential inlet 32 of the vortex chamber 34 through a fixed metering orifice 36, and to the left tangential inlet 38 through an inlet bias valve 40. The central outlet 41 of chamber 34 is connected to the control port 42 of the inspiration valve 20, and also through a DC level valve 44 to a vent 46.

If the pressure applied to the tangential inlets 32, 38 of vortex chamber 34 are approximately equal, an unstable condition is created which causes alternating vortices to form in opposing rotational directions in the chamber 34 at a frequency determined by the volumetric parameters of the chamber 34. The alternation of the vortices causes cyclic pressure variations to occur at the outlet 41. These pressure variations can be used to open and close the inspiration valve 20.

It has been found, in accordance with the present invention, that the frequency of the vortex alternations in the chamber 34 can be changed by connecting a variable volume capacitance to one of the oscillator inlets 32 or 38. This capacitance may take the form of a plurality of tanks such as 50, 52, 54 which can be selectively series-connected by manually operated selector valves 56, 58, or of a piston-adjustable, variable-volume cavity as indicated in container 54.

Figure 2:
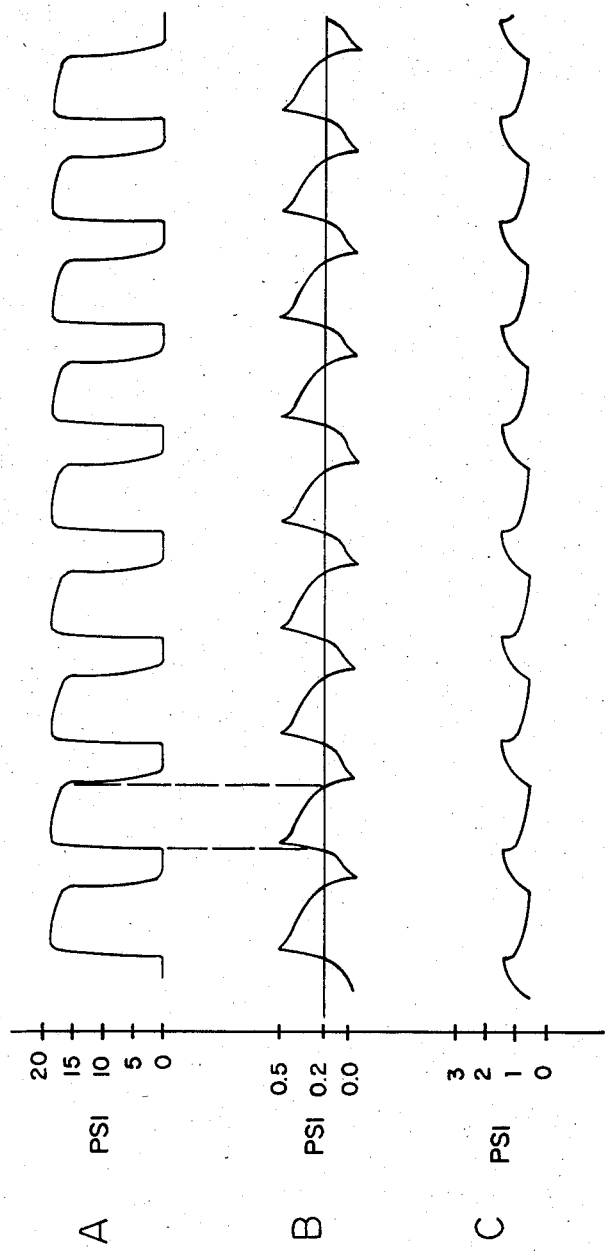
FIGS. 2 through 4 are time-amplitude diagrams showing the pressure variations at various points in the system for various duty cycle settings.
Figure 3:
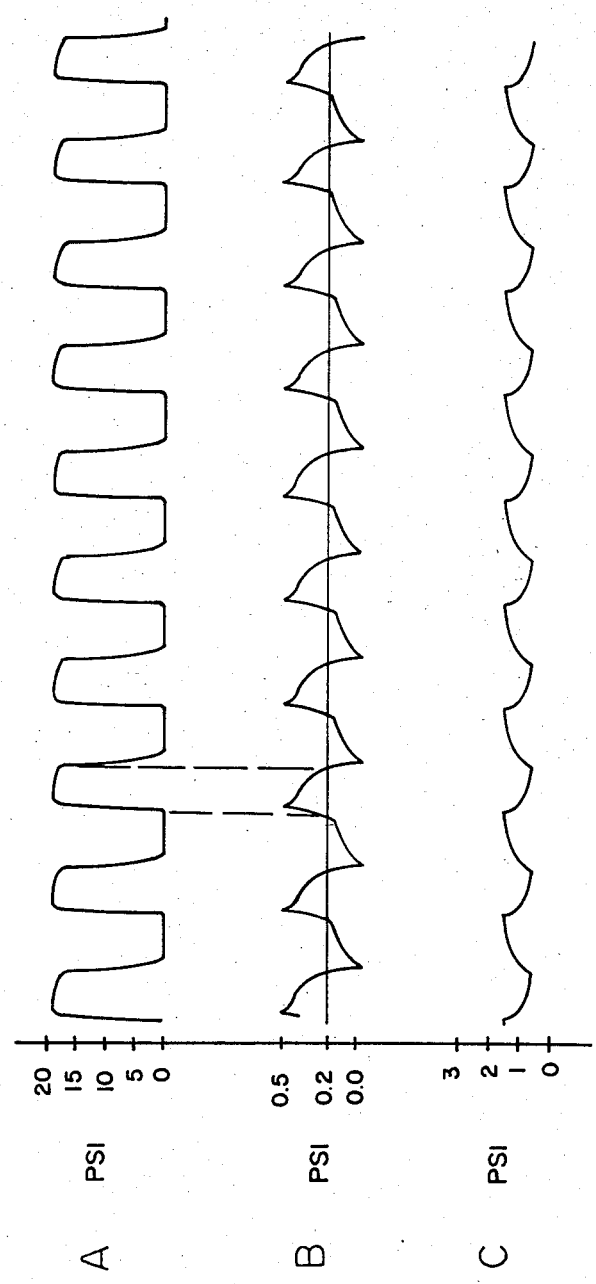
Figure 4:
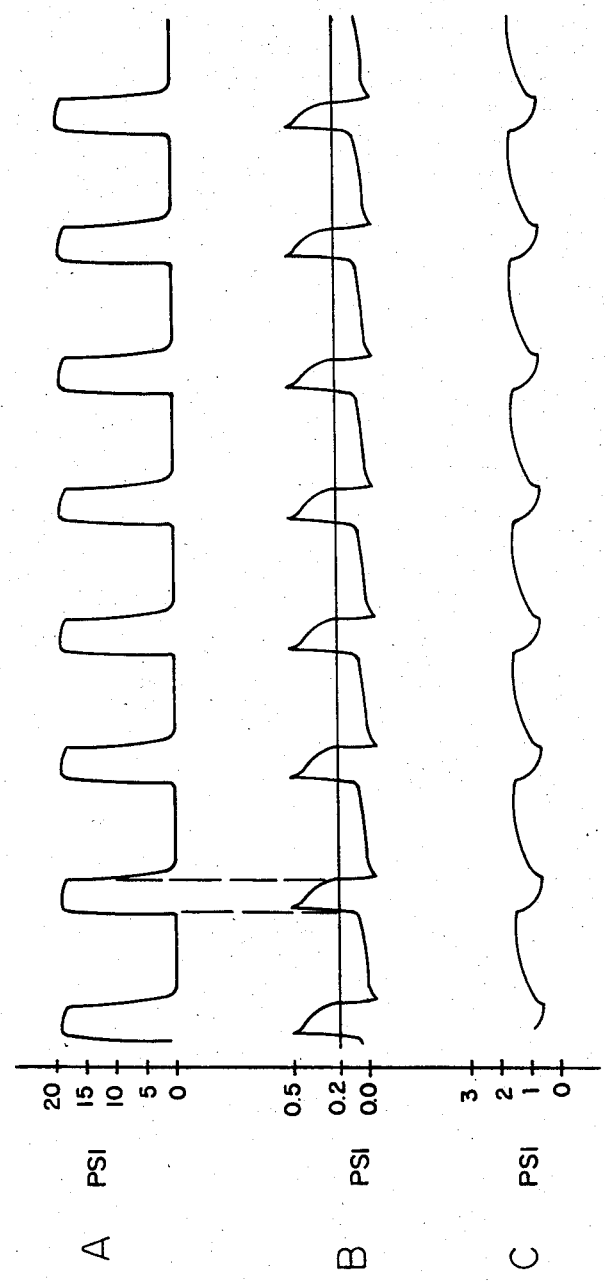

The duty cycle of the inspiration valve 20 can be adjusted in two different ways. The primary adjustment is accomplished by the variable-orifice inlet bias valve 40 which serves to unbalance the pressures applied to the inlets 32, 38. In FIGS. 2 through 4, curves A, B and C represent the pressure variations at the corresponding points of FIG. 1. Specifically, curve B represents the pressure at the outlet 41 of the vortex chamber 34 which controls the inspiration valve 20.

In FIG. 3, showing bias valve 40 at its median setting, it will be noted that the crests and troughs of the curve B are essentially identical. If a pressure of 0.2 PSIG applied to the control port 42 opens inspiration valve 20, the duty cycle of valve 20 (curve A) will be 50%.

FIG. 2 shows the effect of opening the bias valve 40 further. The crests of the curve B become longer, while the troughs become shorter. Consequently, the duty cycle of inspiration valve 20 rises to about 70% in the setting of FIG. 3.

Conversely, a further closing of bias valve 40 lengthens the troughs and shortens the crests of curve B (FIG. 4). Thus, in the setting of FIG. 4, the duty cycle is cut to about 30%.

It will be noted from FIGS. 2-4 that the adjustment of the duty cycle by way of bias valve 40 has some effect on the oscillation frequency. The frequency is at a maximum when the duty cycle is 50% and falls off on either side of that setting—very slightly at first, and then increasingly so towards the ends of the useful duty cycle range. When the range illustrated by FIGS. 2-4 is substantially exceeded, the frequency drops rapidly, and the oscillator eventually stalls.

A secondary control of the duty cycle can be accomplished by adjusting the DC level valve 44. This valve controls, in effect, the DC level of the curve B.

Figure 5:
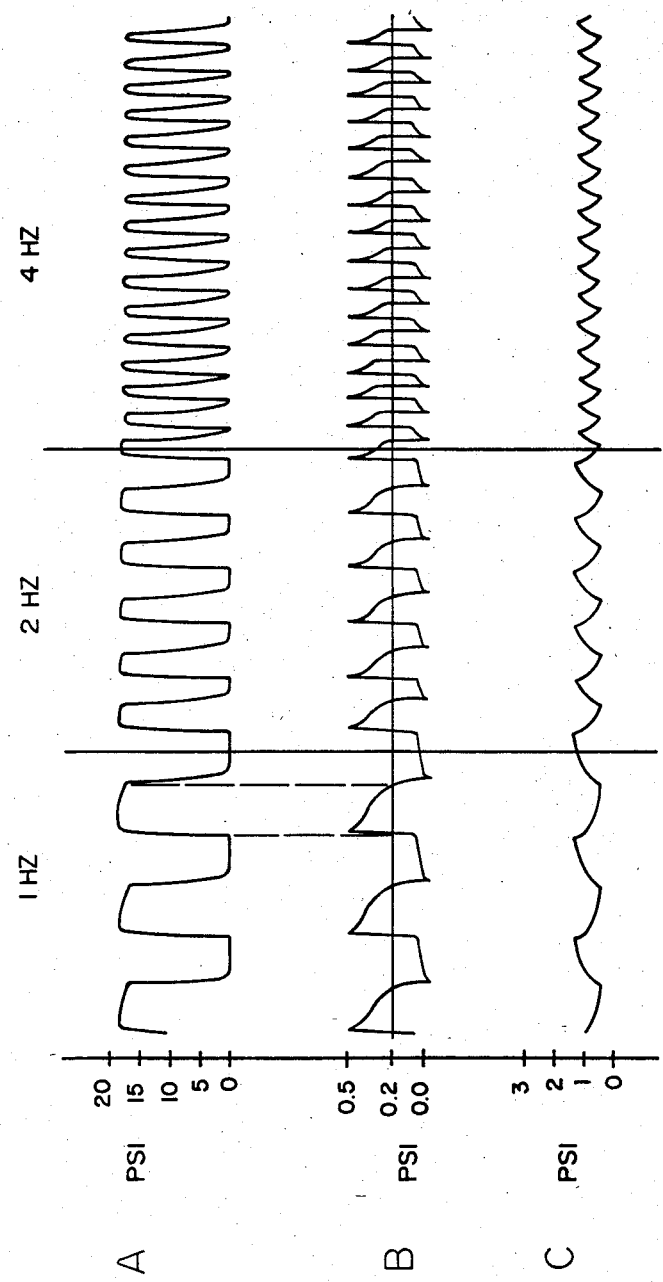
FIG. 5 is a time-amplitude diagram illustrating the pressure variations of FIGS. 2-4 when the frequency is changed.

FIG. 5 shows the effect of changing the frequency of the ventilator 10 from 1 to 2 to 4 Hz by switching the capacitance 52 in and out. It will be noted that the resulting doubling and redoubling of the frequency does not change the shape of curve B, and therefore does not affect the duty cycle setting.

In the preferred embodiment of the invention, an airway port 60 is provided in the trans-tracheal introducer 24 to sense the airway pressure. If the back pressure in the airway exceeds a predetermined threshold (e.g. because of an obstruction in the airway), a vent valve 62 is actuated by the over-pressure to vent the gas lines and thereby stop the jet 22.

Because of the small volume of gas utilized in the oscillator 26, the loss of gas caused by the venting of the oscillator output at 46 is not normally significant.

What is claimed is:

1. In an opposed vortex oscillator having an oscillator chamber and a plurality of fluid inlet conduits, the method of varying the frequency of said oscillator by varying the fluid capacitance of at least one of said inlet conduits.

2. The method of claim 1, in which said fluid capacitance variation is accomplished by selectively connecting at least one tank to said inlet.

3. The method of claim 2, in which a further capacitance variation is accomplished by varying the volume of said tank.

4. In an opposed vortex oscillator switch having an oscillator chamber supplied by a plurality of fluid inlet conduits, and a valve switched between on and off positions depending upon the outlet pressure of said oscillator chamber, the method of varying the on-off ratio of said valve by selectively restricting fluid flow through one of said fluid inlet conduits.

5. In an opposed vortex oscillator switch having a vortex chamber supplied by a plurality of fluid inlets, a partially vented vortex chamber outlet, and a valve controlled by the outlet pressure of said vortex chamber, the method of varying the on-off ratio of said valve by varying the amount of venting of said vortex chamber outlet.

6. In an opposed vortex oscillator having an oscillator chamber supplied by a plurality of fluid inlet conduits, said chamber having a fluid inlet conduit, said chamber having a fluid output which exhibits cyclic pressure variations, the method of varying the wave shape of said pressure variations by selectively restricting fluid flow in one of said fluid inlet conduits.

7. An opposed vortex oscillator comprising:
   (a) an oscillator chamber having a pair of fluid inlets positioned so as to generate fluid vortices in opposing directions;
   (b) a pair of inlet conduit means for supplying fluid under pressure to said fluid inlets;
   (c) fluid capacitance means selectively connectable to at least one of said inlet conduit means for increasing the volume thereof; and
   (d) means for varying said capacitance to control the frequency of said oscillator.

8. The oscillator of claim 7, in which the frequency range of said oscillator is on the order of 1-15 Hz.

9. The oscillator of claim 7, in which said capacitance means include at least one tank.

10. The oscillator of claim 9, further comprising means for varying the volume of said tank.

11. An opposed vortex oscillator switch comprising:
   (a) an oscillator chamber having a pair of fluid inlets positioned so as to generate fluid vortices in opposing directions;
   (b) a pair of inlet conduit means for supplying fluid under pressure to said fluid inlets;
   (c) a fluid outlet from said oscillator chamber, the fluid in said fluid outlet being subject to cyclic pressure variations;
   (d) valve means for controlling the flow of a fluid, said valve means cyclically opening and closing in response to said pressure variations; and
   (e) variable flow restricting means associated with one of said inlet conduit means for selectively varying the fluid flow through said one inlet conduit so as to vary the wave shape of said pressure variations and thereby the on-off ratio of said valve means.

12. A jet ventilator for administering a respiratory gas to a patient, comprising:
   (a) a source of pressurized fluid;
   (b) an opposed vortex oscillator driven by said fluid;
   (c) a fource of pressurized respiratory gas;
   (d) trans-tracheal jet introducer means for introducing said respiratory gas into said patient; and
   (e) a valve interposed between said respiratory gas source and said introducer means, said valve being cyclically switched between an on and an off position by said oscillator to cyclically introduce said respiratory gas into said patient.

13. The jet ventilator of claim 12, further comprising frequency-regulating means interposed between said fluid source and said oscillator for selectively varying the frequency of said oscillator.

14. The jet ventilator of claim 12, further comprising ratio-adjusting means interposed between said fluid source and said oscillator for varying the on-off ratio of said valve.

15. The jet ventilator of claim 12, further comprising ratio-adjusting means interposed between said oscillator and said valve for varying the on-off ratio of said valve.

16. The jet ventilator of claim 12, in which said fluid is said respiratory gas, and said respiratory gas source is also said fluid source.

17. The jet ventilator of claim 12, further comprising safety vent valve means responsive to a pressure buildup in said trans-tracheal introducer means to prevent introduction of respiratory gas into said patient when the patient's airway pressure exceeds a predetermined limit.

* * * * *